US006399066B1

(12) United States Patent
Pier

(10) Patent No.: US 6,399,066 B1
(45) Date of Patent: Jun. 4, 2002

(54) CAPSULAR POLYSACCHARIDE ADHESIN ANTIGEN, PREPARATION, PURIFICATION AND USE

(75) Inventor: Gerald B. Pier, Brookline, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/393,832

(22) Filed: Sep. 10, 1999

Related U.S. Application Data

(62) Division of application No. 08/336,688, filed on Nov. 7, 1994, now Pat. No. 5,980,910, which is a continuation of application No. 08/033,756, filed on Mar. 18, 1993, now abandoned, which is a continuation of application No. 07/727,982, filed on Jul. 10, 1991, now abandoned, which is a division of application No. 07/250,417, filed on Sep. 28, 1988, now Pat. No. 5,055,455.

(51) Int. Cl.$^7$ ............................................... A61K 39/40
(52) U.S. Cl. ............................... 424/165.1; 424/130.1; 424/141.1; 424/150.1; 424/243.1; 530/387.1; 530/388.1; 435/243
(58) Field of Search .................. 530/387.1, 388.1; 424/130.1, 141.1, 150.1, 165.1, 243.1; 435/243

(56) References Cited

U.S. PATENT DOCUMENTS 4,902,616 A * 2/1990 Fournier et al.

FOREIGN PATENT DOCUMENTS

WO          WO 8602358          4/1986

OTHER PUBLICATIONS

Kohler. Science. 1986. 233: 1281–6.*
Milstein, C. Science. 1986. 231–1261–8.*
Yamada, et al., "Possible common biological and immunological properties for detecting encapsulating strains of *Staphylococcus epidermidis*" *J. Clin. Microbiol* (1988) 26(10):2167–72 (Abstract).
Espersen, et al., "Solid–phase radioimmunoassay for IgG antibodies to *Staphylococcus epidermidis*. Use in serious coagulase–negative staphylococcal infections." *Arch. Inter. Med.* (1987) 147(4):689–93 (Abstract).
Espersen, et al., "Enzyme–linked immunosorbent assay for detection of *Staphylococcus epidermidis* antibody in experimental S. epidermidis endocarditis." *J. Clin. Microbiol.* (1986) 23(2):339–42 (Abstract).
Yoshida, et al., "Immunological response to a strain of *Staphylococcus epidermidis* in the rabbit: production of protective antibody." *J. Med. Microbiol.* (1978) 11(4):371–7 (Abstract).
Barsham, et al., "Detection of antibodies to *Staphylococcus epidermidis* in infected total hip replacements by an enzyme linked immunosorbent assay." *J. Clin. Pathol.* (1985) 38(7):839–40.
Vershigora, et al., "Secretory Antibodies to Homologous and Heterologous Staphyloccal Strains in the Colostrum of Rabbits." *ZH Mikrobiol Epidemiol Immunobiol.* 0 (10) (1980) (RECD. 1981) 88–90 (Abstract).
Bernstein, et al., "Antibody coated bacteria in otitis media-awith effusions." *Ann Otol Rhinol Laryngol Suppl* (United States) (1980) 89:104–9. (Abstract).
Nakano, et al., "Polyclonal antibody production in murine spleen cells induced by Staphylococcus." *Microbiol. Immunol.* (Japan) (1980) 24(10) :981–94. (Abstract).
Dobrin, et al., "The role of complement, immunoglobulin and bacterial antigen in coagulase–negative staphylococcal shunt nephritis." *Am. J. Med.* (United States) (1975) 59(5):660–73. (Abstract).

* cited by examiner

*Primary Examiner*—Jennifer E. Graser
(74) *Attorney, Agent, or Firm*—Wolf, Greenfield and Sacks, P.C.

(57) ABSTRACT

A substantially pure capsular exopolysaccharide adhesin of coagulase-negative staphylococcal strains, and a general method to prepare such adhesins, are described. Vaccines composed of such adhesins, and uses of such adhesins to produce polyclonal and monoclonal antibodies against such adhesins, are also disclosed. The adhesins are useful in coating polymeric medical materials to prevent colonization by coagulase-negative staphylococcal strains, and as a probe in selecting desirable polymeric medical materials. Such adhesin antibodies are useful in vivo to prevent infection by nosocomial coagulase-negative staphylococcal strains, in assays for the detection of such bacteria, in assays for the estimation of such adhesins in complex mixtures, and as an affinity chromatography matrix.

5 Claims, 5 Drawing Sheets

FIG.5A
FIG.5B
FIG.5C
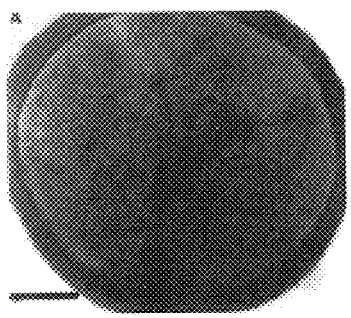
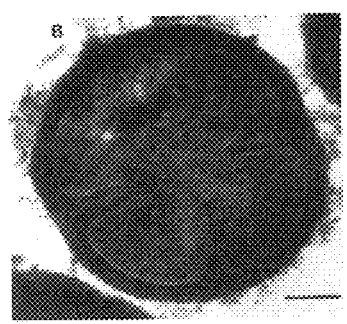
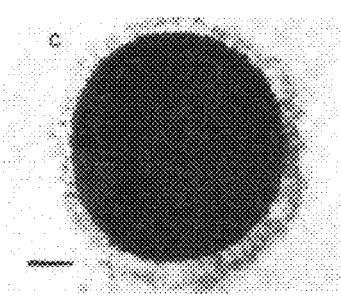
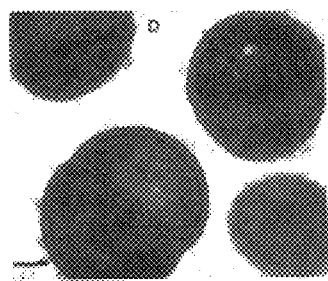
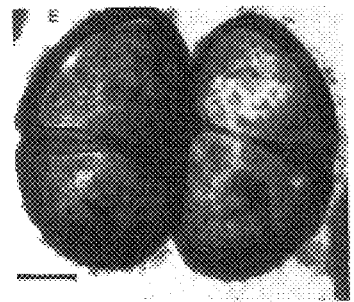
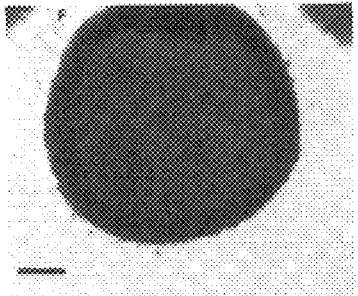
FIG.5D
FIG.5E
FIG.5F

CAPSULAR POLYSACCHARIDE ADHESIN ANTIGEN, PREPARATION, PURIFICATION AND USE

This application is a divisional of U.S. patent application Ser. No. 08/336,688, filed on Nov. 7, 1994, now U.S. Pat. No. 5,980,910 which is a continuation of U.S. patent application Ser. No. 08/033,756 (now abandoned), filed on Mar. 18, 1993, which is a continuation of U.S. patent application Ser. No. 07/727,982 (now abandoned), filed on Jul. 10, 1991, which is a divisional of U.S. patent application Ser. No. 07/250,417, filed Sep. 28, 1988 which is now U.S. Pat. No. 5,055,455. The entire contents of all the foregoing issued patents and patent applications are incorporated by reference herein.

GOVERNMENT SUPPORT

Some aspects of the present invention were made with support by grants from the United States National Institutes of Health (NIH) under NIH contract No. R01-AI23335. The U.S. Government may retain certain rights in the invention.

FIELD OF THE INVENTION

The present invention relates to a substantially pure exopolysaccharide adhesin isolated from a particular strain of *Staphylococcus epidermidis*, to a general method capable of isolating this compound in substantially pure form, and to uses of said purified adhesin product as a vaccine for the production of antibodies effective against the binding of homologous bacterial cells to polymeric materials, and as a probe for the development of polymeric materials useful as catheters and medical prostheses.

DESCRIPTION OF THE BACKGROUND ART

Both *Staphylococcus aureus* (coagulase-positive) and *Staphylococcus epidermidis* (coagulase-negative) have a characteristic propensity for invading skin and adjacent tissues at the site of prosthetic medical devices, including intravascular catheters, cerebrospinal fluid shunts, hemodialysis shunts, vascular grafts, and extended-wear contact lenses. Within 48 to 72 hours, relatively large numbers of staphylococci are demonstrable at the site of insertion of these foreign bodies. Archer, G. L., "*Staphylococcus epidermidis*: The Organism, Its Diseases, and Treatment," in Remington, J. S., et al., eds., *Current Clinical Topics in Infectious Diseases*, McGraw-Hill, New York, 1986, pp. 25–46; Youmans, G. P., et al., *The Biologic and Clinical Basis of Infectious Diseases*, Saunders, Philadelphia, 1985, pp. 618–625, 738–9. It has been demonstrated that *S. epidermidis* cells attach and proliferate on the inner or outer surfaces of catheters, irrespective of their composition (polyethylene, polyvinylchloride, polyvinylfluoride, or polyester based materials).

Although the virulence of coagulase-negative staphylococci clearly is enhanced in the presence of a foreign body, the microbial factor(s) that permit these normal skin commensals to become nosocomial pathogens have not been well characterized. As adherence is believed to be the critical first step in the pathogenesis of coagulase-negative staphylococcal foreign-body infections, attention has focused on surface properties of these organisms that might mediate adherence to, and colonization of, polymeric prosthetic materials.

The most promising candidate for the source of a specific staphylococcal adhesin is an extracellular material often referred to as "slime." It has been hypothesized that the slime substance may protect the *S. epidermidis* cells against antibiotics, as well as against natural host defense mechanisms. Youmans et al., supra; Peters, G., et al., *Journal of Infectious Diseases* 146:479–82 (1982).

It has been known since 1972 that coagulase-negative bacteria isolated from cerebrospinal fluid shunt infections elaborate a mucoid material that stains with alcian blue and is presumably a polysaccharide. Bayston, R., et al., *Developmental and Medical Child Neurology* 14 (Supp. 27):25–8 (1972). The extracellular polysaccharide substance of slime-producing bacteria is a loose amorphous material composed of a range of low and high molecular weight polymers composed, in general, of neutral monosaccharides such as D-glucose, D-galactose, D-mannose, L-fucose, and L-rhamnose, and also contain amino sugars, uronic acid, and polyols such as ribitol and glycerol. Gristina, A. G., *Science* 237:1588–95 (1987). Glucose, galactose, phenylalanine, mannose, hexosamine, phosphorous, glycine and alanine have been found as components of the slime produced by *S. epidermidis* strains in clinical specimens unrelated to biomaterial infections. Ichiman, J., et al., *J. Appl. Bact.* 51:229 (1981). Isolates of such bacteria from sites of infections are more likely to produce slime than are random isolates from skin. Ishak, M. A., et al., *Journal of Clinical Microbiology* 22:1025–9 (1985). Moreover, slime-producing strains adhere well to a variety of polymeric materials. Christensen, G. D., et al., *Infect. Immun.* 37:318–26 (1982).

Coagulase-positive staphylococci (*S. aureus*) are reported to produce multiple cell surface proteins which can be released from such cells by thermal extraction and which can be shown to bind to influenza virus-infected canine kidney cells. It was considered that *S. aureus* produces multiple cell surface protein adhesins. Sanford, B. A., et al., *Infect. Immun.* 52:671–5 (1986); *Proc. Soc. Exp. Biol. Med.* 181:104–11 (1986).

Identification of other microbial adhesins has been reported. Pier (U.S. Pat. No. 4,285,936, Aug. 25, 1981; U.S. Pat. No. 4,528,458, Mar. 25, 1986) discloses a method for partial purification of a polysaccharide antigen from *Pseudomonas aeruginosa* slime. *Escherichia coli* fimbrial protein adhesins have been identified and partially purified by several investigators (Orskov, I., et al., *Infect. Immun.* 47:191–200 (1985); Chanter, H., *J. Gen. Microbiol.* 12:225–243 (1983); Ferreiros, C. M., et al., *Rev. espanol. de fisiolog.* 39:45–50 (1983); and Moch, T., et al., *Proc. Natl. Acad. Sci.* 84:3462–6 (1987)).

Lectin-like glycoprotein adhesins have been identified in the *Bacteroides fragillis* group, and a 70 kDa adhesin has been purified by affinity chromatography (Rogemond, V., et al., *Infect. Immun.* 53:99–102 (1986)). Monoclonal antibody affinity chromatography was used to purify a 165 kDa surface protein of *Mycoplasma pneumoniae* which mediates attachment of such bacteria to target cells (Leigt, D. K., et al., *J. Bacteriol.* 157:678–80 (1984)), and to isolate a 150 kDa adhesin protein from *Streptococcus sanguis* FW213 (Elder, B. L., et al., *Infect. Immun.* 54:421–7 (1986)). A uroepithelial cell adhesin protein of 17.5 kDa was partially purified from fimbrii of *Proteus mirabilis*, a frequent cause of urinary tract infection (Wray, S. K., et al., *Infect. Immun.* 54:43–9 (1986)).

Ludwicka (Ludwicka, A., et al., *Zbl. Bakt. Hyg. A* 258:256–67 (1984)) fractionated by ion-exchange chromatography a phenol-saline extract of slime from *S. epidermidis* and obtained four crude fractions. Both the phenol-saline extract and two of the four crude fractions inhibited the attachment of bacterial cells to polymeric material. On the basis of the presence of monosaccharides in the fractions, the reaction of the fractions with lectins, and the complete inhibition of the production of the four fractions by pretreatment of the bacteria by tunicamycin (inhibitor of glycoprotein synthesis), the authors concluded that the extracellular slime substance is a complex of glycoconjugate (i.e., glycoprotein) character.

Hogt (Hogt, A. H., et al., *Infect. Immun.* 51:294 (1986) have also observed that crude extracellular products from the slime of homologous strains of *S. epidermidis* inhibit the adherence of homologous bacterial cells to polymeric materials used as catheters and prostheses. No information was provided in this report as to the chemical nature of the extracellular products.

Bacterial cells and materials derived from the surface of such cells have been used as vaccines to produce antibodies directed against homologous bacteria. Frank (Frank, R., etal., French Patent Application 85-07315, published Nov. 21, 1986) discloses a covalent conjugate between a capsular protein adhesin (MW-74 kDa) from *Streptococcus mutans* and a polysaccharide from the same (serotypically) organism, and the use of said conjugate as an anti-caries vaccine, Pier (Pier, G. B., et al., U.S. patents, supra) disclose a vaccine comprising a high molecular weight mucoid exopolysaccharide from *Pseudomonas aeruginosa* strain 2192 slime which induces in recipient animals an immunity to said organism. Sadowski (Sadowski, P., U.S. Pat. No. 4,443,549, Apr. 17, 1984; U.S. Pat. No. 4,652,498, Mar. 24, 1984; and EP 82401506.1, published Apr. 27, 1983) discloses monoclonal antibodies specific for surface adhesins of *Escherichia coli* and *Pseudomonas aeruginosa* which may be used for the therapeutic treatment of diseases induced by adhesin-bearing homologous bacteria in humans and animals. Nagy (Nagy, L. K., et al., *Dev. Biol. Stand.* 53:189–97 (1983)) discloses multi-adhesin vaccines for the protection of the neonatal piglet against '*Escherichia coli* infections.

SUMMARY OF THE INVENTION

The inventors considered that, if a substantially pure capsular polysaccharide adhesin antigen could be isolated from the slime of strains of pathogenic *S. epidermidis*, a vaccine could be prepared from such an antigen that could be used to raise polyclonal antibodies in vivo in a human or animal, or monoclonal antibodies in hybridoma cells. Reasoning that adhesin-mediated colonization is required for the onset of pathogenesis, the inventors conceived that the polyclonal or monoclonal antibodies produced against the adhesin of the invention, by preventing the adherence of adhesin-bearing pathogenic bacteria to the recipient's tissue cells or polymeric medical prostheses or catheters, represent a new means for preventing or treating diseases and infections due to *S. epidermidis*.

Further, the substantially pure capsular polysaccharide adhesin of the invention is useful as a probe to test new polymeric materials for medical devices.

Therefore, in a preferred embodiment, the present invention provides a substantially pure polysaccharide from extracts of *S. epidermidis* RP-62 strain (an isolate from a patient with catheterrelated bacteremia that produces copious quantities of slime) that mediates adherence to polymeric materials and also appears to be the capsule for this organism. In another preferred embodiment, the present invention provides a method for producing a substantially pure polysaccharide adhesin from extracts of *S. epidermidis* strain RP-62.

In another preferred embodiment, the substantially pure polysaccharide adhesin of the invention is used as a vaccine to raise in animals antibodies against said adhesin that inhibit the attachment of adhesin-bearing bacteria to polymeric materials.

The substantially pure polysaccharide of the invention may also be used as an antigen to produce monoclonal antibodies in hybridoma cells. Such monoclonal antibodies can be administered for prophylaxis or therapeutic purposes to humans or animals in order to prevent or reduce infections by coagulase-negative staphylococci.

In yet another preferred embodiment, the substantially pure polysaccharide adhesin of the invention is used to screen polymeric materials for resistance to attachment by bacteria.

DESCRIPTION OF THE DRAWINGS

FIG. 5 shows transmission electron microscopy of various strains of coagulase-negative staphylococci following incubation with normal rabbit serum, rabbit serum raised to either whole RP-62A cells or rat antiserum raised to purified adhesin and ferritin-labeled goat antibody to rabbit or rat IgG. A) is strain RP-62 stained with normal rabbit serum (×75,000); B) strain RP-62 stained with rabbit antisera to whole cells (×62,000); C) strain RP-62A stained with rat antiserum to purified adhesin (×48,000); D) strain RP-14 stained with rabbit antiserum to strain RP-62A whole cells (×35,000); E) strain RP-14 stained with rat antisorum to purified adhesin (×65,000); and F) strain RP-62NA stained with rabbit antiserum to strain RP-62 whole cells (×50,000). Bar in each graph represents 200 nm.

DETAILED DESCRIPTION OF THE PREFERRED EMBODIMENTS

Figure 1A:
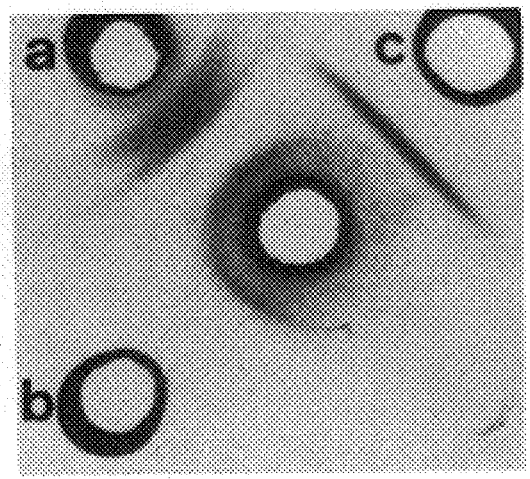
FIG. 1A demonstrates the immunodiffusion pattern of crude extract (A), purified teichoic acid (B) and purified adhesin (C) against antisera raised to whole cells of *S. epidermidis* strain RP-62A.

The invention comprises the isolation in substantially pure form of an exopolysaccharide adhesin antigen from coagulase-negative staphlococci bacteria, use of said adhesin as a vaccine to raise polyclonal and monoclonal antibodies against said adhesin, use of said adhesin to prevent adherence of said bacteria to polymeric materials, and use of said adhesin as a probe to test for polymeric materials to which said bacteria will not adhere.

Materials and Methods

Bacterial Strains

The following strains were provided by Dr. Gordon Christensen, Memphis, Tenn., and have been described previously (Christensen, G. D., et al., *Ann. Intern. Med.* 96:1–10 (1982); Infect. Immun. 37:318–26 (1982)): (a) *Staphylococcus epidermidis* strains RP-62A (slime-producing, highly adherent, from a patient with catheter-related sepsis), RP-62NA (a variant of RP-62A which is less adherent and produces no slime by macroscopic examination), and RP-12; (b) *S. hominis* strain RP-14; and (c) *S. haemolyticus* strain SP-2.

DNA Analysis of *S. epidermidis* Strains

Bacterial cells are lysed by the enzyme lysostaphin. The lysate is digested with RNase A (Sigma) and RNase $T_1$ (Sigma) to degrade bacterial RNA, dissolved in a detergent solution such as sodium dodecyl sulfate, and the proteins digested with proteolytic enzymes such as pronase and proteinase K (Boehringer-Mannheim). DNA is extracted from the digested cells by multiple extractions into phenol, and precipitated from the phenolic solution by the addition of ethanol at −20° C. at a final concentration of 60–70% alcohol. The precipitated DNA is collected by centrifugation, washed with 70% aqueous ethanol, dried in vacuo, then digested with restriction endonucleases (EcoRI, SauIIA, RsaI and ClaI (New England Biolabs, Beverly, Mass.)). The restriction digest is electrophoresed on a 1% agarose gel; restriction fragments are visualized by ethidium bromide staining.

Characterization of Crude Extracts, Purified Adhesin, and Teichoic Acid

Samples are hydrolyzed at 100°C in 6 N HCl from 4 to 48 hours prior to analysis. Reducing carbohydrate content is detected and estimated by the phenol-sulfuric acid reaction (Dubois, M., et al., *Anal. Chem.* 28:350–6 (1956)), proteins by a positive reaction in the Bradford dye test (Bradford, M., *Anal. Biochem.* 72:248–54 (1976)), nucleic acids by absorbance at 254 nm against a DNA standard; phosphate by a positive reaction in the method of Chen (Chen, P. S., et al., *Anal. Chem.* 28:1266 (1956)); lipids by gas-liquid chromatography against fatty acid methyl esters as standards (Lee, J. C., et al., *Infect. Immun.*, in press (1987)); and amino acids and amino sugars by an amino acid analyzer (Model 121 MB, Beckman Instruments, Inc., Fullerton, Calif.) using a lithium citrate system. Monosaccharides are individually identified by gas liquid chromatography of the trimethylsilyl derivatized monosaccharide methyl esters (Chambers, R. C., et al., *Biochem. J.* 125:1009–18 (1971)) in a Hewlett-Packard 5880 instrument using simultaneous injections of identical samples onto 25-foot capillary columns of RSL-310 (Alltech Associates, Deerfield, Ill.) and SP-2330 (Supelco, Delfont, Pa.). The injector and initial oven temperatures are 140° C., which is held for 3 minutes; a 5° C./min rise to 150° C. is then performed, followed by a 30° C./min rise to 210° C., which is then held for an additional 9 minutes. The flame ionization detector is maintained at 250° C. Samples are identified by retention times compared to standards. Serologic analyses can be performed by double diffusion and immunoelectrophoresis methods (Ouchterlony, O., et al., In *Immunochemistry*, Vol. I, Blackwell, Oxford, 1978, Chapter 19).

Adherence Assays

The adherence of coagulase-negative staphylococcal strains to polymeric (i.e., silastic) catheter tubing (French 3, Jesco International Inc., San Antonio, Tex.) is determined as follows. An overnight culture of bacteria in tryptic soy broth is diluted to contain $10^6$ colony-forming units (cfu)/ml. A 3 cm length of tubing fitted with a 21 gauge needle and sterilized with ethylene oxide gas is then dipped into the culture for 15 min at room temperature. The tubing is washed in saline by vigorously agitating the tubing, as well as repeatedly drawing saline through the tubing with a 3 ml syringe fitted to the needle. Washing is continued until wash fluids contain less than 1 cfu/100 $\mu$l. This occurs in about 3 separate washes. After discarding a 1 cm section of the tubing, bacteria adhering to the remaining 2 cm is quantified by rolling the tubing over the surface of a tryptic soy agar plate in several directions, followed by overnight incubation at 37° C. The cfu/catheter are counted the next day. The efficiency of the transfer of bacteria from plastic tubing to the agar plate can be estimated by radio-labelling the organisms by including one $\mu$Ci of [$^{14}$C]-sodium acetate in the preliminary overnight culture medium. The number of cfu adhering to the tubing before and after rolling on the agar plate is determined by liquid scintillation counting and correlated with bacterial counts obtained by plating identical samples.

Direct adherence of the purified adhesin to catheter tubing is determined by incubating a 0.5 cm length of tubing with a 0.5 mg/ml solution of adhesin in 40 mM phosphate buffer, pH 7.2, for two hours at 37° C., washing the tubing in phosphate-buffered saline 0.05% Tween 20, and performing a standard ELISA or RIA assay on the sensitized piece of tubing (Bryan, L. E. et al. *J. Clin. Microbiol.* 18:276–82 (1983)). By the term "ELISA" is intended an enzyme-linked immunoassay. By the term "RIA" is intended a radioimmunoassay.

Inhibition of adherence of bacteria to catheter tubing by crude extracts and purified adhesin is performed by incubating the catheter tubing in solutions of these materials for two hours at 37° C., washing the coated tubing in sterile saline, placing it in bacterial cultures ($10^6$ cfu/ml), and completing the adherence assay as described supra. When poorly adherents strains of *S. epidermidls* (e.g., strains CL and SP-2) are used in inhibition assays, the input inoculum should be increased to $10^7$ cfu/ml, which increases the number of adhering bacteria as much as 5-fold. Inhibition of adherence is calculated as follows:

$$\% \text{ inhibition} = 100 - \frac{(100)(\text{no. of cfu adhering following adhesin treatment})}{\text{no. of cfu adhering without treatment}}$$

Inhibition of adherence by rabbit antibody to purified adhesin (see infra) is performed by incubating the bacteria with the indicated concentration of normal and immune serum for 2 hr at 4° C., washing the bacteria three times in tryptic soy broth, resuspending to $10^6$ cfu/ml tryptic soy broth, and continuing the adherence assay as described supra. Inhibition of adherence is calculated as follows;

$$\% \text{ inhibition} = 100 - \frac{(100)(\text{no. of cfu adhering with immune serum})}{\text{no. of cfu adhering with normal serum}}$$

Inhibition data should be statistically analyzed for significance by Students t test.

Transmission Electron Microscope

Transmission electron microscopy of *S. epidermidis* strains is performed as previously described (Pier, GB, *J. Clin. Microbiol.*, 24:189–96 (1986). For visualization of extracellular structures, bacterial cells are incubated with either a 1:2 dilution of rabbit antibody to whole cells or undiluted rat antibody raised to purified adhesin (see infra), or with normal serum controls. After three saline washes, bacteria are incubated with ferritin-conjugated antibody to either rabbit or rat IgG.

Preparation of Crude Bacterial Extracts

Crude extracts are prepared by incubation of cell suspensions with the enzymes lysostaphin and lysozyme. Insoluble material is removed by sequential centrifugation and filtration through a micropore filter (0.45 $\mu$m), the filtrate is dialyzed against water, and then lyophilized (freeze-dried in vacuo at low temperature).

Isolation of Adhesin

Eighteen-hour cultures of *S. epidermidis* strains are subjected to thermal shock (95–100° C.) at about pH 5.0. The mixture is brought to neutral pH (preferably 6.8) and room temperature, then clarified by sequential centrifugation and passage through a micropore filter. The clear extract is concentrated, neutralized, and the conductivity reduced (preferably to below 10 millisiemans) by repeated ultrafiltration through a 10,000 dalton cut-off membrane and washing with water. The retained concentrate, which contains macromolecules of mass greater than 10,000 daltons, is then fractionated by ion-exchange chromatography at neutral pH (preferably about 7.0); a preferred system is DEAE Zeta-Prep 250 cartridge (LKB Instruments, Rockville, Md.). Adhesin is eluted by 0.2 M NaCl at neutral pH (preferably about 7.0), as determined by an adherence assay (infra). Adhesin-containing fractions are then subjected to affinity chromatography on a Concanavalin A-Sepharose column (LKB Instruments) to remove a mannan containment that is contributed by the original bacterial tryptic soy broth growth medium and that co-purifies with the bacterial polysaccharide adhesin. The unbound fraction is repeatedly dialyzed against water to remove salts and small molecules, then lyophilized. After reconstitution of the adhesin-containing powder in calcium-containing buffer at an acidic pH (preferably 5.0), the solution is incubated sequentially with DNase (to remove contaminating DNA), RNase (to remove contaminating RNA), and pronase (to remove contaminating protein). The purified adhesin solution is then fractionated on a molecular sieve column in an ammonium carbonate buffer at neutral pH (preferably about 7.0). Elution is monitored by measuring $A_{206}$ nm; adhesin fractions eluting with a Kav of 0.0–0.2 are collected and pooled. This fraction contains substantially pure capsular polysaccharide adhesin.

Isolation of Teichoic Acid

Teichoic acid, another component of the slime of *S. epidermidis*, is recovered from the DEAE Zeta Prep 250 ion-exchange column used in fractionating adhesin, in the fraction eluting with a higher concentration (0.6 M) of NaCl than eluted adhesin (0.2 M). This material is then digested with nuclease enzymes as described above, protein is denatured by heating at 100° C., at an acid pH (preferably about 4.0), then chromatographed on a molecular sieve column (Sepharose CL-4B) in ammonium carbonate buffer at neutral pH. Serologically-active fractions that elute with a Kav of 0.33–0.57 are pooled, dialyzed, and lyophilized.

Adhesin Vaccine

Polyclonal Antibodies

Polyclonal antibodies to epitopic regions of the purified adhesin may be raised by a plurality of injections of said adhesin antigen into a host animal. In a preferred embodiment, antibodies are produced in rabbits by subcutaneous administration of 0.5 mg of antigen in complete Freund's adjuvant, followed 7 days later by intravenous injections three times weekly with 0.5 mg of antigen in saline. The thrice weekly injections are performed for 3 consecutive weeks, and blood is then drawn 5 days after the last injection. Normal (pre-immune) serum is obtained in all cases.

Polyclonal antibodies to purified adhesin may also be raised in rats given three 50 $\mu$g injections five days apart, with blood drawn 5 days after the final injection.

Polyclonal antibodies to whole cells of *S. epidermidis* strains are raised in rabbits as previously described (Pier, G. B., et al., *J. Infect. Dis.* 147:494–503 (1983)).

Monoclonal Antibodies

Monoclonal antibodies are immunoglobulins directed to specific epitopic regions on an antigen. Monoclonal antibodies against the substantially pure polysaccharide adhesin of the invention can be produced by the hybridoma technology of Köhler and Milstein (Köhler, G., *Science* 23:1281–6 (1986); Milstein, C., *Science* 21:1261–8 (1986)).

Briefly, the purified adhesin is used to once-prime or hyperimmunize animal donors of antibody-producing somatic B cells (e.g., lymphocytes). Lymph nodes and spleens of immunized animals are convenient sources. Although mouse and rat lymphocytes give a higher percentage of stable fusions with mouse myeloma lines, the use of rabbit, human and frog cells is also possible. In a preferred embodiment, hyperimmunized mouse spleen cells are used to make the fused cell hybrids.

Specialized myeloma cell lines are available for use in hybridoma-producing fusion procedures (Kohler, G., et al., *Eur. J. Immunol.* 6:511–9 (1976); Schulman, M., et al., *Nature* 276:269–70 (1978)). Methods for generating hybrids of anti-adhesin antibody producing spleen or lymph node cells and myeloma cells usually comprise mixing somatic cells with myeloma cells in a 10:1 proportion (though the proportion can vary from 20:1 to 1:1, respectively) in the presence of an agent(s) that promotes fusion. It is preferred that the same species of animal is the source of both the somatic and myeloma cells. Fusion methods have been described by Köhler and Milstein (Köhler, G., et al., *Nature* 256:495–7 (1975); *Eur. J. Immunol.* 6:511–19 (1976)), in which Sendai virus is the fusion agent, and by Gefter (Gefter, S., et al., *Somatic Cell Genet.* 3:231–6 (1977)), in which polyethylene glycol is the fusion agent. In a preferred embodiment, the method of Gefter et al. is modified to include dimethylsulfoxide as an additional fusion agent.

Isolation of clones and antibody detection are carried out by standard techniques. Fusion cell hybrids are selected by culturing the cells on media that support growth of hybridomas but prevent the growth of unfused myeloma cells. (The unfused somatic cells do not maintain viability in in vitro cultures and hence do not pose a problem.) In a preferred embodiment, myeloma cells lacking hypoxanthine phosphoribosyltransferase (HPRT⁻) are used. These cells are selected against in a hypoxanthine/aminopterin/thymidine (HAT) medium in which hybridoma cells survive due to the HPRT⁺ genotype of the spleen cells, but unfused myeloma cells do not. Myeloma cells with different genetic deficiencies that can be selected against in media supporting the growth of genotypically competent hybrids are also possible.

The detection of anti-adhesin antibody-producing hybrids can be achieved by any one of several standard assays, including ELISA and RIA techniques that have been described in the literature (Kennet, R., et al., eds., *Monoclonal Antibodies, Hybridomas: A New Dimension in Biological Analysis*, Plenum, New York, 1980, pp. 376–84; Bryan, L. E., et al., *J. Clin. Microbiol.* 18:276–82 (1983)).

Once the desired fused cell hybrids have been selected and cloned into individual anti-adhesin antibody-producing cell lines, each cell line may be propagated in either of two standard ways: injection of the hybridoma into a histocompatible animal and recovery of the monoclonal antibodies in high concentration from the body fluids of the animal (e.g., serum or ascites fluid), or propagation in vitro in tissue culture, wherein the antibody in high concentration is recoverable from the culture medium.

Therapeutic Use of Anti-Adhesin Antibody

Monoclonal antibodies specific to epitopic regions on the colonization-mediating adhesin, as well as the non-specific polyclonal antibodies described above, can be used clinically for the prevention or treatment of diseases caused by pathogenic bacteria producing and bearing such adhesins. For example, polyclonal and monoclonal antibodies specific for the capsular polysaccharide adhesin of the present invention can be administered to any animal species for the prevention and/or treatment of infections due to pathogenic *Staphylococcus epidermidis*, e.g., those that colonize polymeric implanted medical devices and catheters. By the term "administer" is intended, for the purpose of this invention, any method of treating an animal with a substance, such as orally, intranasally, or parenterally (intravenously, intramuscularly, or subcutaneously). By the term "animal" is intended any living creature that is subject to staphlococcal infection, including humans, farm animals, domestic animals, or zoological garden animals.' The mode of administration of these antibodies is preferably parenteral. The antibodies may be suspended or dissolved in any of several suitable liquid vehicles and delivered to the patient by any one of several parenteral means. In some instances, and particularly where human treatment is involved, purification may be desired or required pursuant to government regulations. Provided the antibody is present in a pharmacologically effective dosage, other liquid compositions are also pharmaceutically effective, including mixtures of antibodies and skim milk and/or antibodies in aqueous salt solutions of serum albumin. In humans, the antibody may be preferably administered in parenteral form, though any compatible carrier may be used. Of course, the dosage administered will be dependent upon the age, health, and weight of the recipient, kind of concurrent treatment, if any, frequency of treatment, and the nature of the effect desired. Preferably, the dosage should result in a concentration of at least about one Ag of specific antibody per milliliter of blood.

Diagnostic Use of Anti-Adhesin Antibody

The adhesin-specific antibodies are also useful for medical and research purposes. For example, the antibodies can be used diagnostically to detect with great accuracy the presence of *Staphylococcus epidermidis* strains among a general population of bacteria. Other applications include the use of adhesin-specific monoclonal antibodies in affinity chromatography systems for the purification of *Staphylococcus epidermidis* polysaccharide adhesin or in assay systems for the quantitative estimation of such adhesin.

Use of Purified Adhesin as a Probe

The purified capsular polysaccharide adhesin of the invention can be used in conjunction with the adherence assays described supra as a probe in designing new polymeric materials to which coagulase-negative staphlococci bacteria will not adhere. Such new polymers would be extremely beneficial to patients in whom catheters and other medical prosthetic devices and shunts are employed and who now suffer from the nosocomial effects of such bacteria.

Having now described the invention in general term, the following specific examples will serve to illustrate more fully the nature of the present invention, without acting as a limitation upon its scope.

EXAMPLE I

Isolation of Strain PR-62A Adhesin

*Staphylococcus epidermidis* RP-62A was grown in 15 l of tryptic soy broth in an LSL Biolaffite fermentor with aeration (0.5 l/min), stirring (200 rpm), and maintenance of the pH at 7.2 by titration with 50% acetic acid and 5 NaOH. After 18 hr growth at 37° C., the pH was adjusted to 5.0 with 50% acetic acid and the temperature of the culture raised to 95–100° C. for 1 h. After cooling, the pH was adjusted to 6.8, the culture removed from the fermentor, and bacterial cells removed by centrifugation. The supernatant was passed through a 0.5µ filter and then concentrated to about 400 ml on a Pellicon ultrafiltration system (Millipore Corp., Bedford, Mass.) using membranes with a molecular weight cut-off of 10,000 dalton. The supernatant was then diluted with 2 l deionized water and reconcentrated to 400 ml. This step was repeated until the pH of the solution was 6.8 and the conductivity was around 4.8 millisiemens. A portion (¼) of the solution was then applied to a DEAE Zeta-prep 250 cartridge (LKB Instruments, Rockville, Md.) previously equilibrated in 0.05 M Tris buffer, pH 6.8. After loading, the cartridge was washed with 600 ml of 0.05 N Tris buffer and the eluate discarded. The adhesin was then recovered in the fraction eluting with 0.2 N NaCl in 0.05 M Tris buffer, after preliminary assays determined that this molarity of NaCl eluted material which inhibited the adherence of strain RP-62A to silastic catheter tubing (see infra). The 0.2 M NaCl eluate was pooled, dialyzed against numerous changes of deionized water, and lyophilized. The material was then resuspended in 0.1 M sodium acetate, pH 6.0, at 25 mg/ml. and chromatographed on an affinity column of Concanavalin A-Sepharose (LKB Instruments) to remove a mannan component from the tryptic soy broth medium which co-purified with the adhesin. The unbound adhesin-containing fraction was recovered, dialyzed against numerous changes of deionized water, and lyophilized. The material was then dissolved (25 mg/ml) in 0.1 M NaOH, 1.0 mM $MgCl_2$, and 1.0 mM $CaCl_2$, pH 5.0, and digested with DNase (1 mg/ml) and RNase (3 mg/ml) for 16 hr at 37° C., after which time pronase (1.0 mg/ml) was added and an additional 4 hr digestion at 37° C. carried out. This solution was then applied to a 2.6×90 cm column of Sepharose CL-4B (Pharmacia Fine Chemicals, Piscataway, N.J.) equilibrated in 0.2 M ammonium carbonate, pH 6.8. Fractions (8 ml) were collected, and pools were made from fractions absorbing UV light at 206 nm that eluted with a $K_{av}$ of 0.0–0.2 (peak=0.02).

EXAMPLE II

Isolation of Strain PR-62A Teichoic Acid

Teichoic acid was recovered from the Zeta-prep 250 cartridge in the fraction eluting with 0.6 M NaCl. This material was digested with nuclease enzymes as described above, heated at 100° C., pH 4.0, for 1 h, then chromatographed on a 2.6×90 cm column of Sepharose CL-4B in 0.2 M ammonium carbonate. Serologically active fractions eluting with a Kav of 0.33–0.57 (peak=0.48) were pooled, dialyzed against deionized water, and lyophilized.

EXAMPLE III

Chemical Components of Crude Extract, Teichoic Acid Fraction of Slime, and Purified Adhesin Utilizing the methodology described above, a fraction isolated from the culture supernatant of *S. epidermidis* strain RP-62A that appeared to have the properties of an adhesin was analyzed. The chemical components of the crude extract, the isolated teichoic acid, and the purified adhesin are shown in Table 1.

TABLE 1

Chemical Components Identified in Crude Extract, Teichoic Acid, and Purified Adhesin of *Staphylococcus epidermidis* strain RP-62A

| | Preparation | | |
|---|---|---|---|
| Component | Crude Extract | Teichoic Acid | Purified Adhesin |
| Reducing sugar | 12* | 20 | 54 |
| Amino sugars | 5 | 25 | 20 |
| Uronic acids | 2 | <1** | 10 |
| Phosphate | 11 | 14 | <0.02** |
| Protein | 3 | 2 | 1 |
| Nucleic acids | 7 | 1 | 1 |
| Lipids | <0.01** | <0.01** | <0.01** |
| Unidentified | 60 | 38 | 14 |
| Monosaccharides (percent of total sugars) | | | |
| Glycerol | | 20 | <0.1** |
| Glucose | | 20 | <0.1** |
| Galactose | | <0.1** | 22 |
| Glucosamine | | 10 | 15 |
| Galactosamine | | <0.1** | 5 |

*Percent of total weight.
**Lower limit of detection.

Crude extract contained numerous components, of which carbohydrate and phosphate were predominant. The teichoic acid fraction of slime was composed principally of phosphate, glycerol, glucose, and glucosamine. The purified adhesin was principally composed of carbohydrate with only low to non-detectable levels of protein, nucleic acids, and phosphate. No lipids were detected in the purified adhesin. The principal monosaccharides identified were galactose, glucosamine and galactosamine, glucose was absent. In addition, a complex chromatogram of monosaccharides indicated the presence of galacturonic and glucuronic acids, as well as smaller amounts of mannosamine, fucosamine, and neuraminic acid. Trace amounts of ribose and muramic acid were identified, likely due to low level contamination with RNA and peptidoglycan.

EXAMPLE IV

Figure 1B:
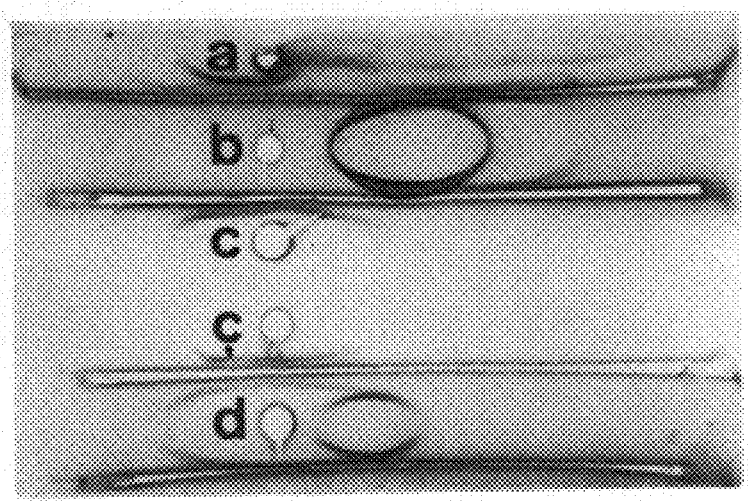
FIG. 1B demonstrates immunoelectrophoresis of *S. epidermidis* antigens. Troughs were filled with antisera to strain RP-62A whole cells. A, crude extract; B, teichoic acid, C, purified adhesin; D, mixture of teichoic acid and purified adhesin.

Serological Properties of Crude Extract, Teichoic Acid, and Purified Adhesin Serologically, crude extract gave three precipitin lines in double diffusion when tested against a rabbit antisera raised against whole cells of strain RP-62A (FIG. 1A), while teichoic acid and the purified adhesin gave single precipitin lines. By immunoelectrophoresis (FIG. 1B), the crude extract had multiple precipitin lines against antisera to whole cells. In contrast, purified adhesin gave a single precipitin line which did not move in the electric field. Purified teichoic acid gave a strong precipitin line migrating towards the anodal end of the gel, as well as a weaker, more negatively charged line when high concentrations of antigen were used. A mixture of teichoic acid and purified adhesin resulted in two precipitin lines corresponding to the individual, purified components.

EXAMPLE V

Adherence of S. Epidermidis Strains to Polymeric Tubing

The adherence assay described supra was used to quantify the binding of strains of coagulase-negative staphylococci to silastic catheter tubing. When the inoculant size of strain RP-62A was varied from $10^2$–$10^9$ cfu/ml, linear binding was obtained between input inocula of $10^3$–$10^6$ cfu/ml. When $10^6$ cfu/ml of radiolabeled bacteria were used in this adherence assay, and pieces of catheter tubing counted before and after being rolled over the tryptic soy agar plate, 67–75% of the counts were dislodged in three separate experiments, indicating that a majority of the adherent bacterial population was being measured by this technique.

Strains of coagulase-negative staphylococci were screened in the adherence assay at inocula of $10^6$ cfu/ml. Three highly adherent strains of coagulase-negative staphylococci in addition to strain RP-62A (strains RP-12, RP-14, F-3284), and poorly adherent strains (Table 2).

TABLE 2

Expression of Slime and Adhesin, and Adherence of Coagulase-Negative *Staphylococci* to Silastic Catheter Tubing

| | | Production of: | | Mean No. CFU |
|---|---|---|---|---|
| Strain | Species | Slime[1] | Adhesin | Adhering (±SD) |
| RP-62A | S. epidermidis | +++ | Pos[2] | 233 ± 20 |
| RP-12 | S. epidermidis | +++ | Neg | 295 ± 40 |
| RP-14 | S. hominis | + | Pos | 167 ± 24 |
| F-3284 | S. epidermidis | ++ | Pos | 144 ± 3 |
| RP-62NA | S. epidermidis | − | Pos[3] | 68 ± 30 |
| SP-2 | S. haemolyticus | − | Neg | 7 ± 7 |
| CL | S. haemolyticus | − | Neg | 19 ± 5 |

[1]Semi-quantitative measurement as described by Christensen, G. D., et al. Infect. Immun. 37:318–26 (1982).
[2]Presence (Pos) or absence (Neg) of adhesin determined by double immunodiffusion.
[3]Strain RP-62NA is only weakly positive for adhesin production.

Of the three additional highly adherent strains, two expressed an antigen giving a precipitin line of identity in double diffusion with the purified adhesin of strain RP-62A, while two of the poorly adherent strains expressed no detectable antigen. The adherence properties of strain RP-62NA were also evaluated in the adherence assay (Table 2). Strain RP-62NA adhered only about ⅓ as well as its parent strain, and a weak precipitin line corresponding to purified adhesin could be detected by 'immunodiffusion only if culture super-natants of strain RP-62NA were concentrated 10-fold.

Figure 2:
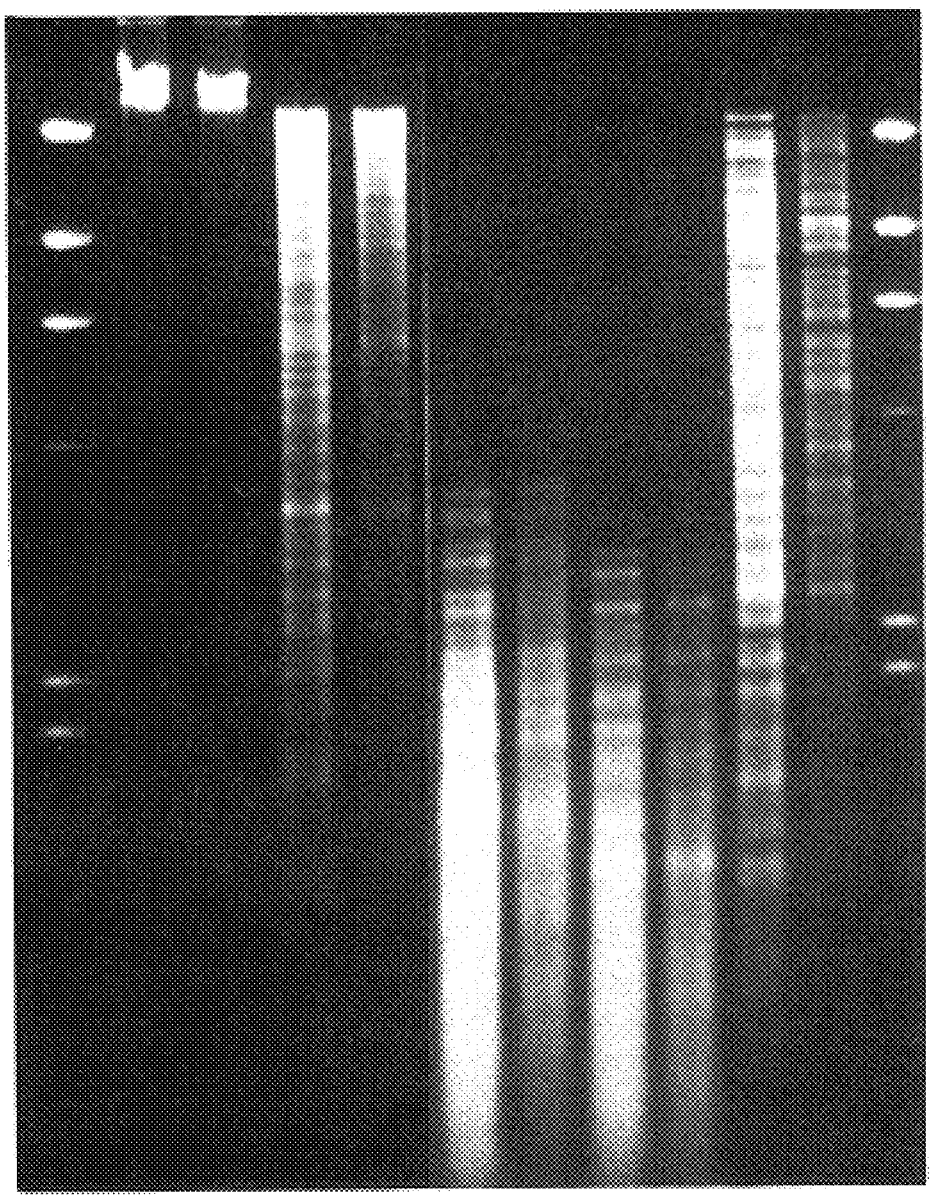
FIG. 2 demonstrates the electrophoresis pattern of restriction enzyme digests of bacterial DNA from strains RP-62A (left-hand pattern of each pair) and RP-62NA (right-hand pattern of each pair). Lanes 1 and 12, HindIII digest of phage lambda DNA; Lanes 2 and 3, undigested DNA from RP-62A and RP-62NA; Lanes 4 and 5, EcoRI digest; Lanes 6 and 7, SauIIIA digest; Lanes 8 and 9, RsaI digest; Lanes 10 and 11, ClaI digest.

Restriction enzyme digestion of total cellular DNA of strains RP-62A and RP-62NA indicated that the parent strain and its variant were closely related, as the digestion patterns using four different restriction enzymes were identical (FIG. 2).

EXAMPLE VI

Properties of Purified Adhesin

Figure 3:
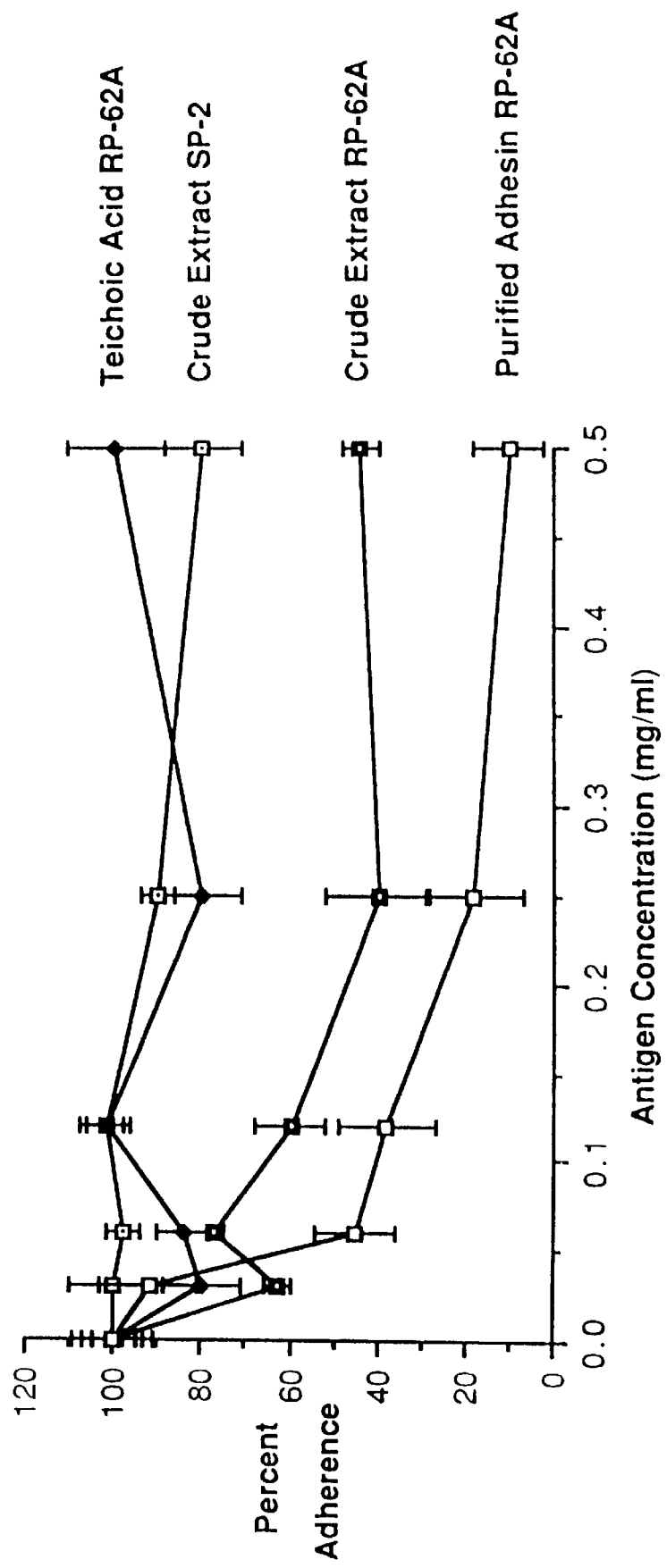
FIG. 3 demonstrates the inhibition of binding of *S. epidermidis* strain RP-62 cells to silastic catheter tubing after incubation of the tubing in the indicated concentrations of the various bacterial antigens prior to dipping in bacterial suspension ($10^6$ cells per ml). Significant (p<0.05, t test) inhibition was seen only with crude extracts from strain RP-62A at concentrations of 0.12–0.50 mg/ml and with purified adhesin at concentrations of 0.06–0.50 mg/ml.
Figure 4:
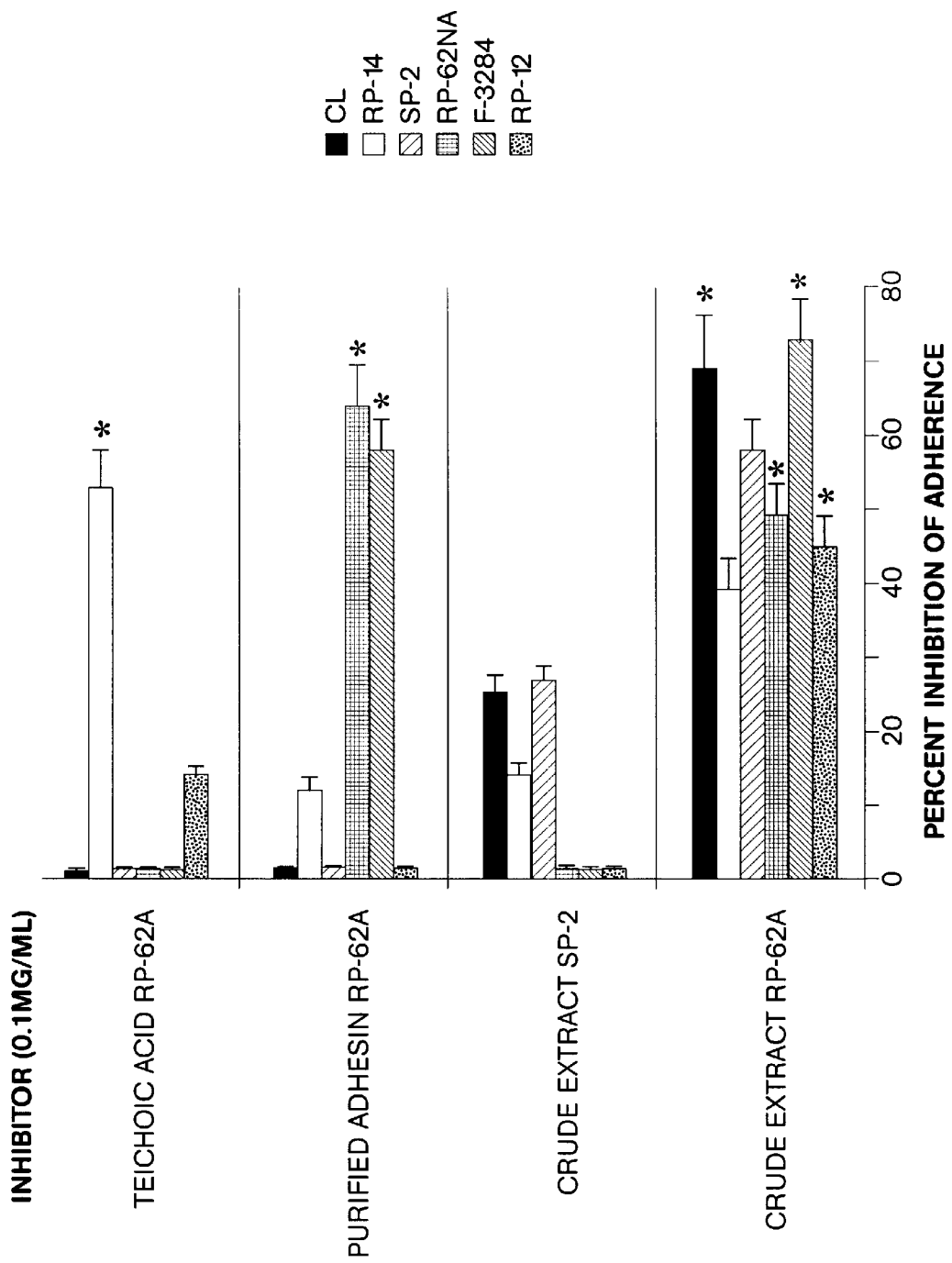
FIG. 4 demonstrates the inhibition of adherence of various strains of coagulase-negative staphylococci to silastic catheter tubing by different antigen preparations (0.1 mg/ml concentration) from *S. epidermidis* strain RP-62A. An asterisk indicates significant (p<0.05, t test) inhibition.

The adhesin purified from S. epidermidis strain RP-62A was tested for its ability to inhibit adherence of the homologous strain to silastic catheter tubing. A dose-related inhibition of adherence was seen with both crude extract and purified adhesin prepared from strain RP-62A (FIG. 3). Teichoic acid did not inhibit adherence of strain RP-62A, nor did the extract from the poorly adherent strain SP-2, prepared in a manner identical to that of crude extract from strain RP-62A. When these same materials (0.1 mg/ml) were tested for their ability to inhibit adherence of other strains of coagulase-negative staphylococci to silastic catheter tubing, only the two strains expressing the adhesin antigen were significantly (P<0.05, t test) inhibited from adhering by purified adhesin (FIG. 4). Some of the strains were inhibited from adhering to the catheter material by crude extract from strain RP-62A, and adherence of strain SP-2 was inhibited by teichoic acid from strain RP-62A. In a similar fashion, rabbit antibodies raised to strain RP-62-A-purified adhesin from strain RP-62A inhibited the adherence of this strain in a dose-related fashion at serum concentrations of $\geq 0.25\%$. Using a serum concentration of 1%, there was significant (P<0.05, t test) inhibition of adherence of strains of coagulase-negative staphylococci expressing the adhesin antigen, while antigen-negative strains were not inhibited from adhering to silastic catheter tubing at this serum concentration (Table 3).

TABLE 3

Inhibition of Adherence of Coagulase-Negative *Staphylococci* to Silastic Catheter Tubing by Rabbit Antibody to Adhesin Purified from *Staphylococcus epidermidis* Strain RP-62A

| Strain | Percent Inhibition of Adherence (±1 SD)[1] |
|---|---|
| Adhesin positive | |
| RP-62A | 59 ± 17* |
| RP-14 | 53 ± 1* |
| F-3284 | 65 ± 14* |
| RP-62NA[2] | 1 ± 13 |
| RP-12[3] | 62 ± 8 |
| Adhesin negative | |
| SP-2 | 17 ± 9 |
| CL | 0 |

[1]Serum concentration 1%.
[2]p < 0.05, t test.
*Produces greatly reduced amount of adhesin.
[3]Initial studies with RP-12 were negative. However, more recent studies have shown that RP-12 does in fact produce this adhesin. Apparently, the sera used initially failed to detect the production of adhesin from strain RP-12.

Silastic catheter tubing coated with the purified adhesin readily bound rabbit antibodies raised to whole cells and purified adhesin, while antibodies in pre-immunization sera had only a slight reaction with coated catheter tubing (Table 4).

TABLE 4

Reaction of Rabbit Antibody to Purified Adhesin from Strain *Staphylococcus epidermidis* RP-62A with Silastic Catheter Tubing Cather Coated with Purified Adhesin

| | Reaction with: | |
|---|---|---|
| Serum (5% Concentration) | Uncoated Catheter | Adhesin-Coated Catheter |
| Pre-immune | 0.150* | 0.202 |
| Immune to | | |
| Whole cell | 0.191 | 1.212 |
| Purified adhesin | 0.076 | 1.443 |

*Mean $A_{405}$ of triplicate wells containing indicated catheter.

EXAMPLE VII

Transmission Electron Microscopy

Transmission electron microscopy was used to examine the appearance of bacterial cells of RP-62A, RP-62NA, RP-14, RP-12 and CL after treatment with normal rabbit or rat serum, rabbit antiserum raised to whole RP-62A cells, and rat antiserum raised to purified adhesin. Both of these antisera revealed an extracellular structure surrounding strains RP-62A and RP-14 that appeared to be a capsule (FIGS. 5A–D) which was not seen with normal serum (shown in the figure only for normal rabbit serum and strain RP-62A; all other strains treated with any normal serum looked identical to FIG. 5A). Strain RP-62NA appeared to have only a slight amount of capsular material when reacted with antibodies to whole cells (FIG. 5F) and purified adhesin (not shown), consistent with the serologic findings mentioned supra. Both strains RP-12 and CL lacked any detectable capsule using sera to RP-62A whole cells and purified adhesin (not shown).

The invention now being fully described, it will be apparent to one of ordinary skill in the art that many changes and modifications can be made thereto without departing from the spirit or scope of the invention as set forth herein.

What is claimed as new and desired to be secured by LETTERS PATENT OF THE UNITED STATES:

1. A method of producing monoclonal antibodies against a substantially pure coagulase-negative bacterial capsular polysaccharide adhesin of *Staphylococcus epidermidis* that binds to polymeric material comprising: propagating a hybridoma formed by fusing a cell capable of producing antibodies against said adhesin with a myeloma cell and harvesting the antibodies produced by said hybridoma, wherein said adhesin inhibits at a concentration of about 0.1 mg/ml, binding to said polymeric material of at least about 50% of cells of *Staphylococcus epidermidis* RP-62A, RP-62NA or F-3248.

2. A composition comprising a monoclonal antibody that binds to a substantially-pure coagulase-negative bacterial capsular polysaccharide adhesin of *Staphylococcus epidermidis* that binds to polymeric material, wherein said adhesin inhibits at a concentration of about 0.1 mg/ml, binding to said polymeric material of at least about 50% of cells of *Staphylococcus epidermidis* RP-62A, RP-62NA or F-3284.

3. A monoclonal antibody preparation comprising a monoclonal antibody that binds to an adhesin obtained from a *Staphylococcus epidermidis* RP-62A culture using the Isolation of Strain RP-62A Adhesin procedure comprising the following steps:

(a) extracting adhesin from cultures of said bacterial strain RP-62A;

(b) digesting the adhesin;

(c) chromatographically separating said adhesin extract of (a) on an ion-exchange column;

(d) eluting a capsular polysaccharide from the column of (c) which binds to silastic materials and inhibits binding of Staphylococcus epidermidis RP-62A, RP-62-NA, and F-3284 to said polymeric materials;

(e) chromatographically separating the capsular polysaccharide adhesin-containing fractions from (d) on an affinity column; and (f) further purifying the capsular polysaccharide adhesin by chromatographing the adhesin-containing fractions from (e) on a molecular sieve column, and collecting material eluting between Kav of 0.0 to about 0.2.

4. A pharmaceutical composition comprising the monoclonal antibody of claim 3 and a pharmaceutically compatible carrier.

5. A hybridoma for producing the monoclonal antibody of claim 3 made by a process comprising the step of fusing:

a) a cell capable of producing antibodies against the adhesin obtained from a *Staphylococcus epidermidis* RP-62A culture using the Isolation of Strain RP-62A Adhesin procedure comprising the following steps:

(i) extracting adhesin from cultures of said bacterial strain RP-62A;

(ii) digesting the adhesin;

(iii) chromatographically separating said adhesin extract of (i) on an ion-exchange column;

(iv) eluting a capsular polysaccharide from the column of (iii) which binds to silastic materials and inhibits binding of Staphylococcus epidermidis RP-62A, RP-62-NA, and F-3284 to said polymeric materials;

(v) chromatographically separating the capsular polysaccharide adhesin-containing fractions from (iv) on an affinity column; and (vi) further purifying the capsular polysaccharide adhesin by chromatographing the adhesin-containing fractions from (v) on a molecular sieve column, and collecting material eluting between Kav of 0.0 to about 0.2, and b) a myeloma cell.

* * * * *